(12) United States Patent
Meadows

(10) Patent No.: US 7,211,510 B2
(45) Date of Patent: May 1, 2007

(54) STACKING CIRCUIT ELEMENTS

(75) Inventor: Paul Milton Meadows, Glendale, CA (US)

(73) Assignee: Advanced Bionics Corporation, Valencia, CA (US)

( * ) Notice: Subject to any disclaimer, the term of this patent is extended or adjusted under 35 U.S.C. 154(b) by 238 days.

(21) Appl. No.: 10/937,149

(22) Filed: Sep. 9, 2004

(65) Prior Publication Data

US 2006/0051896 A1    Mar. 9, 2006

(51) Int. Cl.
*H01L 21/44* (2006.01)
*H01L 29/40* (2006.01)
*H01L 23/52* (2006.01)
*H01L 23/48* (2006.01)
*H01L 21/768* (2006.01)

(52) U.S. Cl. ............ 438/667; 438/668; 257/621; 257/774; 257/E21.597

(58) Field of Classification Search ............ 438/667, 438/668; 257/621, 774, 686, E21.597, E23.174
See application file for complete search history.

(56) References Cited

U.S. PATENT DOCUMENTS

| | | | | |
|---|---|---|---|---|
| 4,258,468 A | * | 3/1981 | Balde | 29/830 |
| 4,394,712 A | * | 7/1983 | Anthony | 361/779 |
| 4,897,708 A | * | 1/1990 | Clements | 257/690 |
| 5,585,675 A | | 12/1996 | Knopf | |
| 5,606,710 A | | 2/1997 | Hall et al. | |
| 5,986,209 A | | 11/1999 | Tandy | |
| 6,166,328 A | | 12/2000 | Tandy | |
| 6,188,021 B1 | | 2/2001 | Tandy | |
| 6,207,474 B1 | | 3/2001 | King et al. | |
| 6,213,747 B1 | | 4/2001 | Tandy | |
| 6,265,660 B1 | | 7/2001 | Tandy | |
| 6,329,221 B1 | | 12/2001 | King et al. | |
| 6,351,028 B1 | | 2/2002 | Akram | |
| 6,380,629 B1 | | 4/2002 | Kim | |
| 6,566,232 B1 | * | 5/2003 | Hara et al. | 438/455 |
| 6,596,634 B2 | * | 7/2003 | Umetsu et al. | 438/666 |

* cited by examiner

*Primary Examiner*—Luan Thai
(74) *Attorney, Agent, or Firm*—Bryant R. Gold; Albert Kau; Travis K. Laird

(57) ABSTRACT

A method of stacking dice in an electronic circuit includes controlling a size of a hole made in a connection pad on each die of said dice to selectively provide an electrical connection to a particular die in the stack. Additionally, a method of stacking dice in an electronic circuit includes forming holes in each of the dice, and providing electrical connection material selectively at some of the holes to provide for selective electrical connections among the dice. A stack of dice in an electronic circuit includes a number of dice stacked on top of each other, each die in the stack having one or more holes therein, conductive material extending through the holes and making electrical connection between one or more of the dice in the stack and the electronic circuit. An implantable stimulator with a stack of pulse generator integrated circuits (ICs) includes a number of pulse generator ICs stacked on top of each other, each IC having a number of holes formed therein, wherein the holes are aligned, and conductive material extending through the holes and making electrical connection between one or more of said ICs in the stack and an electronic circuit of the stimulator.

7 Claims, 6 Drawing Sheets

STACKING CIRCUIT ELEMENTS

BACKGROUND

Many devices can benefit from optimization of space required for electronic modules, which may allow miniaturization of the device itself and/or introduction or enlargement of other device components. Compact electronic modules are particularly useful for devices requiring volume efficiency, including medical devices and consumer electronics devices. For instance, optimization of the packaging of an electronic module in a transistor radio would allow the entire radio to be more compact. Alternatively or additionally, the freed-up space could be used by other components, such as a larger battery. As another example, the size of implantable medical devices is preferably minimized to reduce trauma, cosmetic, and other effects of a device located in the body. Optimization of the packaging of an electronic module in an implantable medical device would allow the device to be smaller and/or allow the device to accommodate additional and/or larger components.

For example, implantable microstimulators known as Bion® devices are characterized by a small, cylindrical housing which contains electronic circuitry that produces electric currents between spaced electrodes. These microstimulators are implanted proximate to target tissue, and the currents produced by the electrodes stimulate the tissue to reduce symptoms or otherwise provide therapy for various disorders. A compact electronic module would allow a Bion device to be smaller and thus easier to implant and less noticeable and/or allow the device to accommodate additional and/or larger components, such as a larger rechargeable battery that would lengthen time between recharges.

Radio-frequency powered and battery powered microstimulators are described in the art. See, for instance, U.S. Pat. No. 5,193,539 ("Implantable Microstimulator"); U.S. Pat. No. 5,193,540 ("Structure and Method of Manufacture of an Implantable Microstimulator"); U.S. Pat. No. 5,312,439 ("Implantable Device Having an Electrolytic Storage Electrode"); U.S. Pat. No. 6,185,452 ("Battery-Powered Patient Implantable Device"); U.S. Pat. No. 6,164,284 and U.S. Pat. No. 6,208,894 (both titled "System of Implantable Device for Monitoring and/or Affecting Body Parameters"). The '539, '540, '439, '452, '284, and '894 patents are incorporated herein by reference in their entirety.

Microstimulators to prevent and/or treat various disorders are taught, e.g., in U.S. Pat. No. 6,061,596 ("Method for Conditioning Pelvis Musculature Using an Implanted Microstimulator"); U.S. Pat. No. 6,051,017 ("Implantable Microstimulator and Systems Employing the Same"); U.S. Pat. No. 6,175,764 ("Implantable Microstimulator System for Producing Repeatable Patterns of Electrical Stimulation"); U.S. Pat. No. 6,181,965 ("Implantable Microstimulator System for Prevention of Disorders"); U.S. Pat. No. 6,185,455 ("Methods of Reducing the Incidence of Medical Complications Using Implantable Microstimulators"); and U.S. Pat. No. 6,214,032 ("System for Implanting a Microstimulator"). The techniques described in these additional patents, including power charging techniques, may also be used with the present inventions. The '596, '017, '764, '965, '455, and '032 patents are incorporated herein by reference in their entirety.

A number of the above cited patents describe microstimulator designs and methods for manufacturing a microstimulator or portions of a microstimulator. Disclosed herein are improved designs and techniques for producing compact electronic modules for a microstimulator or other medical or non-medical device. In addition, the designs and methods disclosed allow such devices, to be manufactured more efficiently, more reliably, and/or more cost effectively.

SUMMARY

A method of stacking dice in an electronic circuit includes controlling a size of a hole made in a connection pad on each die of said dice to selectively provide an electrical connection to a particular die in the stack. Additionally, a method of stacking dice in an electronic circuit includes forming holes in each of the dice, and providing electrical connection material selectively at some of the holes to provide for selective electrical connections among the dice.

A stack of dice in an electronic circuit includes a number of dice stacked on top of each other, each die in the stack having one or more holes therein, conductive material extending through the holes and making electrical connection between one or more of the dice in the stack and the electronic circuit.

An implantable stimulator with a stack of pulse generator integrated circuits (ICs) includes a number of pulse generator ICs stacked on top of each other, each IC having a number of holes formed therein, wherein the holes are aligned, and conductive material extending through the holes and making electrical connection between one or more of said ICs in the stack and an electronic circuit of the stimulator.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

To reduce volume and surface area in an electronic circuit, it is desirable to be able to stack circuit elements on top of each other. In particular, it would help decrease the footprint and increase the density of an electronic circuit to be able to stack integrated circuit dice on top of each other within a larger electronic circuit. As indicated above, such conservation of space may be valuable in a wide variety of applications, including medical implants, in which device volume is a precious commodity.

A die (plural, dice) is an integrated circuit that is manufactured on a semiconductor wafer or substrate. A large number of identical integrated circuits are typically formed on a single semiconductor wafer. Then, the portion of the wafer supporting each individual integrated circuit is cut or etched away from the wafer to form the individual integrated circuit dice. An integrated circuit die is typically designed to be used in a larger electronic circuit on a circuit board or substrate.

In many applications, a die is packaged or enclosed after manufacture and provided with external connections for connecting the integrated circuit inside the die package to the larger electronic circuit of which it is a part. A packaged die is often referred to as a chip. However, dice are sometimes left unpackaged and then glued or otherwise secured directly on the substrate or circuit board of a larger circuit. The unpackaged die is then wire bonded to electrically interconnect the integrated circuit on the die to the larger circuit of which it is a part. Such a die is sometimes referred to as a chip-on-board. When attempting to save space by stacking integrated circuits, it may be advantageous to use unpackaged die in the stack. Otherwise, the packaging will significantly increase the height of the stack.

Although it is advantageous to save space by stacking dice in a circuit, it then becomes difficult to selectively make wire-bond connections to particular die layers in the stack. Consequently, each stacked die may be made smaller than the die upon which it sits, with extra connection pads being provided for the sole purpose of providing a mechanism for making interconnections from one stacked die to the next with typical wire-bonds. However, this means that each die in the stack has to be individually designed and manufactured to a particular size and that similar or identical dice cannot be stacked.

To overcome these limitations, the present specification provides a method of stacking integrated circuit dice in a larger electronic circuit, where the stacked dice can be of the same size and geometry and connections can be readily and selectively made to any or all of the circuits in the stack. This method will now be described and specific examples will be given with reference to the figures.

Figure 1:
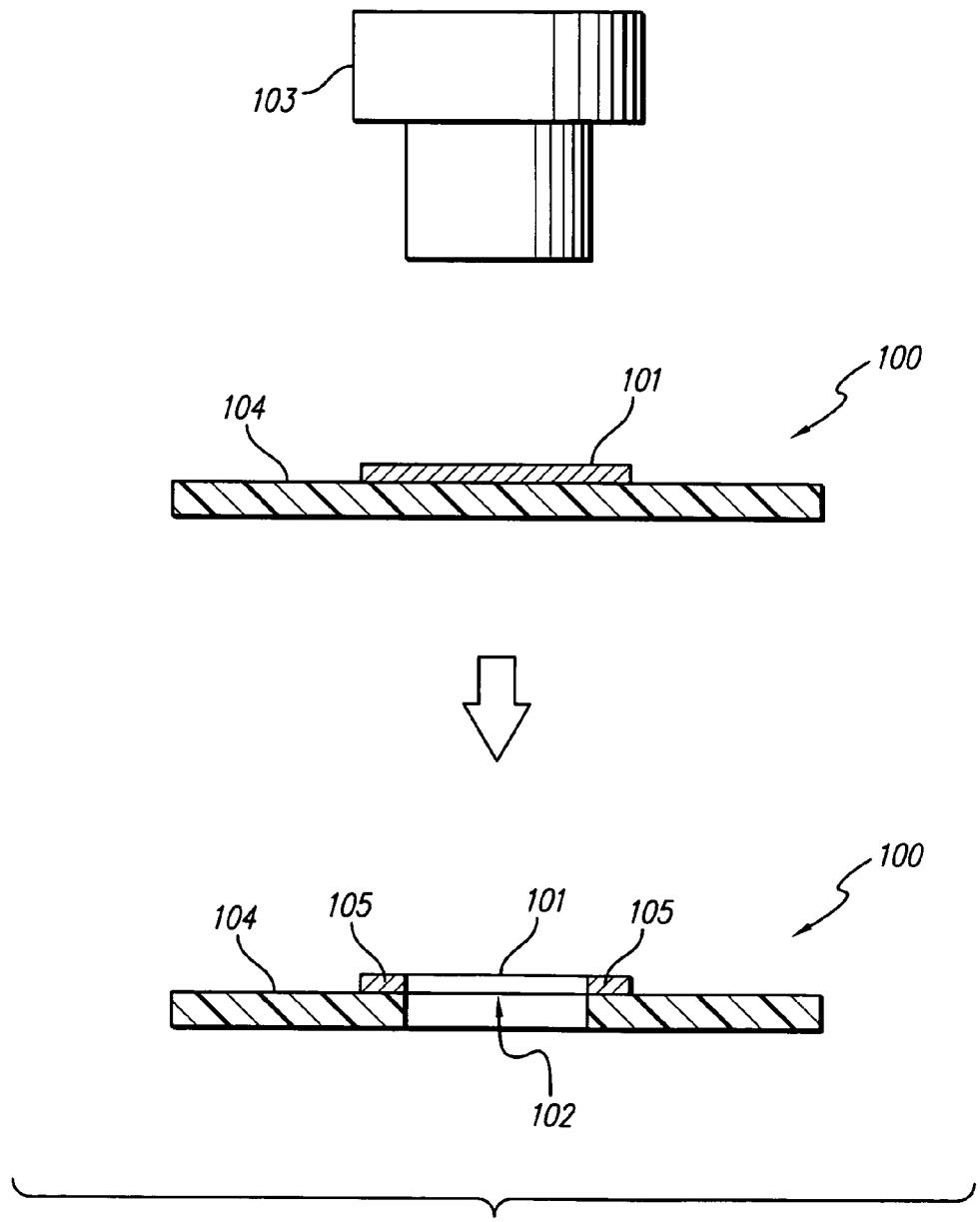
FIG. 1 is an illustration of a method of drilling a hole through a connection pad of an integrated circuit to allow for selective connections to various circuits in a stack according to principles described herein.

FIG. 1 is an illustration of a method of drilling a hole through a connection pad of an integrated circuit die to allow for selective connections to various circuits in a stack according to principles described herein. As shown in FIG. 1, an integrated circuit die (100) includes a substrate (104) on which the circuitry of the integrated circuit die (100) is formed. That circuitry includes, and is electrically connected to, a connection pad (101).

The connection pad (101) is formed on the substrate (104) of a metal or other conductive material and is used to make a connection between the other circuitry on the substrate (104) and a larger circuit in which the integrated circuit die (100) is incorporated. For example, a connection wire could be bonded to the connection pad (101) and to the larger circuit of which the die (100) is a part to electrically connect the die (100) to the larger circuit. This has been the typical use of the connection pad (101).

However, as will be described herein, if the integrated circuit die (100) is to be used in a stack of dice to conserve space, a hole (102) is instead drilled through the connection pad (101) and the underlying substrate (104) of the integrated circuit (100). A drill (103) is used to drill the hole (102) through the connection pad (101) and underlying substrate (104). The drill (103) may be, for example, a laser or other means of drilling a hole of selective diameter through the connection pad (101) of the die (100).

In the example of FIG. 1, the hole (102) through the connection pad (101) is smaller than the connection pad (101) itself. Thus, as seen in the bottom portion of FIG. 1, a ring (105) of the conductive connection pad material remains around the hole (102). It should be appreciated that, by varying the size of the hole (102) drilled through the connection pad (101), a larger or smaller ring of (105) of connection pad material will remain. In fact, if the hole (102) drilled is larger than the connection pad (101), the connection pad (101) will be completely ablated or removed from the substrate (104) by the drilling. It is by adjusting the size of the hole (102) drilled through the connection pad (101) that it becomes possible to control which layers of a stack of integrated circuit dice are electrically connected through a vertical connection in the stack to the substrate and to the larger circuit supporting the stack.

It will also be appreciated that the same effect can be obtained by first drilling holes in the integrated circuits and then selectively applying electrical connection material around the holes based on where electrical connections are to be made. Such electrical connection material can be any conductive material that electrically connects conductive material extending through the hole to the integrated circuit.

Figure 2:
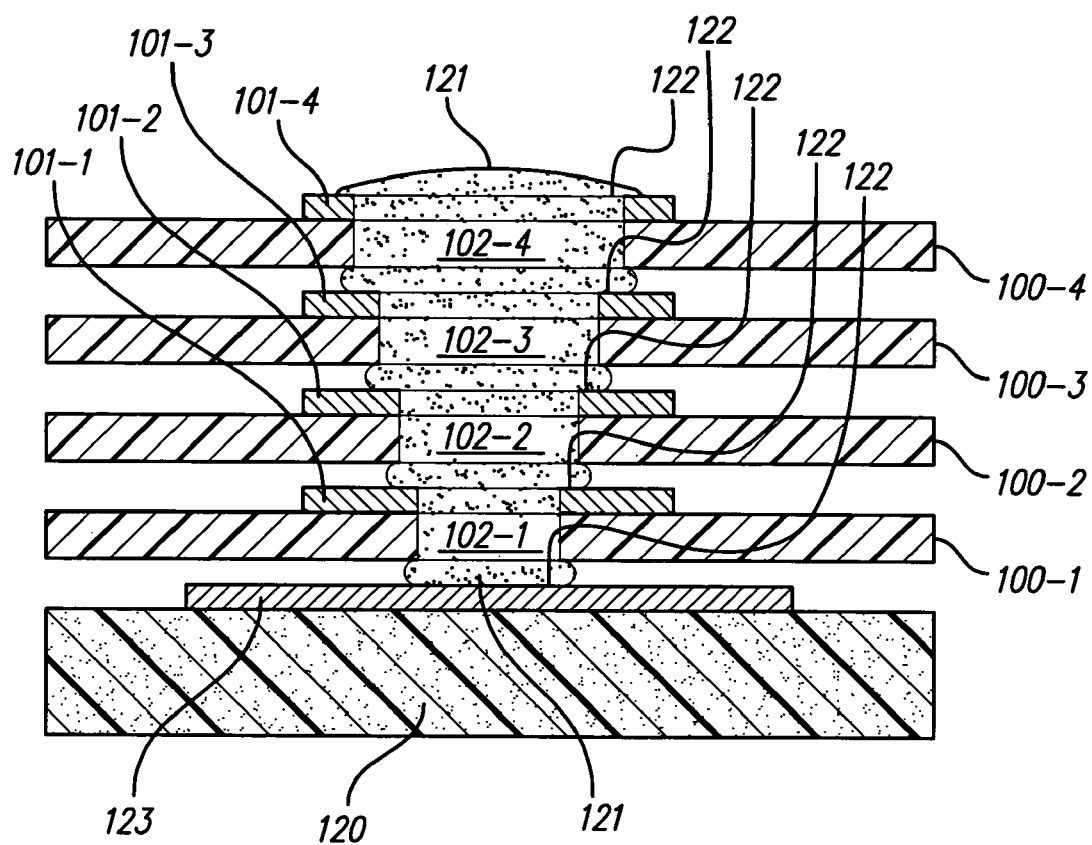
FIG. 2 is an illustration of a stack of integrated circuits where each circuit in the stack is connected to a common electrode on a substrate according to principles described herein.

FIG. 2 is an illustration of a stack of integrated circuit dice, where each die in the stack is connected to a common electrode on an underlying substrate according to principles described herein. As shown in FIG. 2, four dice (100, 100-1 to 100-4) are stacked on a substrate (120). The substrate or circuit board (120) supports a larger circuit of which the stacked dice (100) are a part.

In the exemplary connection of FIG. 2, each of the dice (100) is to be connected to an electrode (123) of the larger circuit on the substrate (120). The dice (100) may be identical or of the same size or geometry.

The connection between the four dice (100) and the electrode (123) is made by drilling holes (102, 102-1 to 102-4) of varying size in the connection pads (101, 101-1 to 101-4) of the stacked dice (100). The dice (100) are then stacked with the holes (102) in the dice (100) being registered or aligned. Next, the registered holes (102) are filled with a conductive material (121), such as a conductive epoxy. As the conductive epoxy fills the pathway formed by the aligned holes (102) in the dice (100), the conductive epoxy (121) provides an electrical connection between the connection pad (101) on each die (100) and the electrode (123) on the substrate (120).

As shown in FIG. 2, the higher up in the stack a particular die (100) is, the larger the hole (102) drilled through the connection pad (101) of that die is. Thus, the hole (102-4) in the top die (100-4) is the largest hole in the stack. However, the hole (102-4) in the top die (100-4) is still smaller than, and within, the connection pad (101-4) on that die (100-4).

The hole (102-3) in the next die (100-3) down in the stack is smaller than the hole (102-4) in the die (100-4) above. The hole in the next die (100-2) down is smaller still. This trend continues to the bottom die (100-1) which has the smallest hole (102-1) through its connection pad (101-1).

With this configuration, when a conductive epoxy (121) is introduced into the aligned holes (102), the epoxy (121) will cascade down the steps formed by the decreasing width of the holes (102). Thus, at each level, the conductive epoxy (121) makes contact (122) with the ring of the connection pad (101) that remains around the hole (102) in each respective die (100).

At the bottom of the stack, the conductive epoxy (121) makes contact and electrical connection with the electrode (123) on the substrate (120). In this way, the conductive epoxy (121) provides an electrical connection between the connection pad (101) on each of the stacked dice (100) and the electrode (123) on the substrate (120). It will be appreciated that while the illustrated example shows four stacked dice (100), the same technique could be applied with more or fewer dice in the stack.

Figure 3:
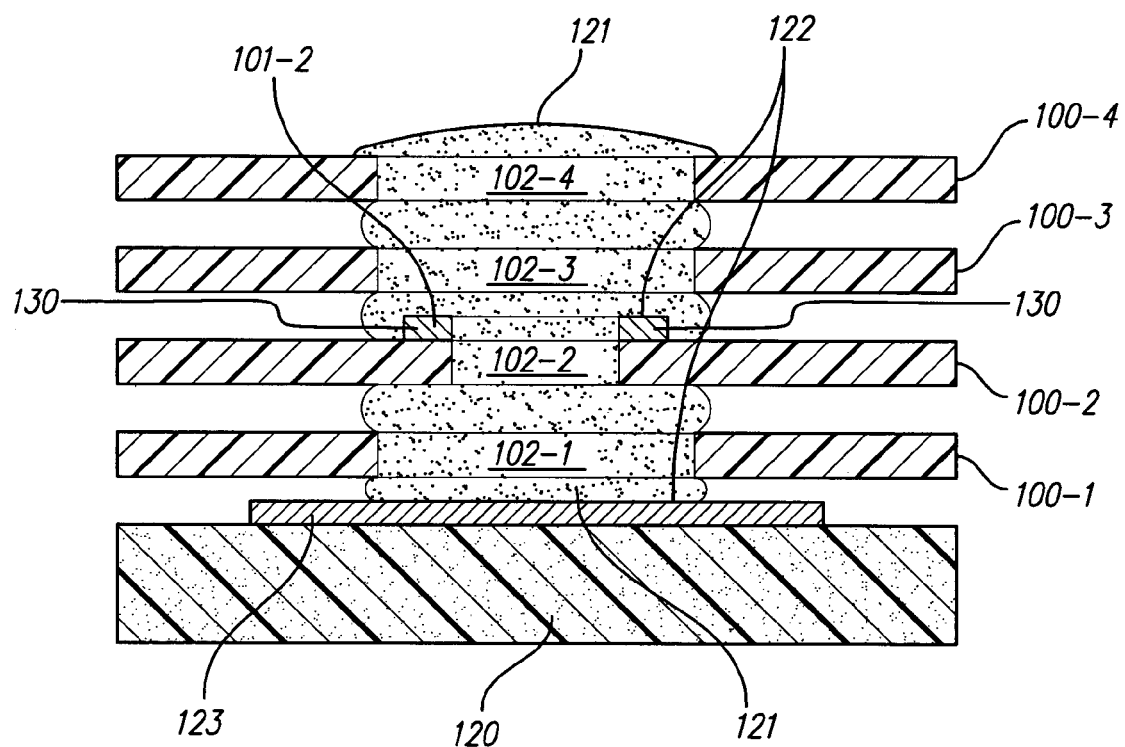
FIG. 3 is an illustration of a stack of integrated circuits where only one of the circuits in the stack is selectively connected to an electrode on an underlying substrate according to principles described herein.

While it may be desired to connect each die in a stack to an underlying electrode, it will also regularly be the case that only one, or less than all, of the dice in a stack should be connected to an underlying electrode. In other words, in some cases, it will be desired to selectively connect a particular die in the stack to the larger circuit on the underlying substrate without also connecting to the other dice in the stack. FIG. 3 is an illustration of a stack of integrated circuits where only one of the circuits in the stack is selectively connected to an electrode on an underlying substrate according to principles described herein.

In the example of FIG. 3, only the second die in the stack, die (100-2) is to be connected to the electrode (123) on the substrate (120). Consequently, the holes (102) in the dice (100) in FIG. 3 are not progressively smaller, as in FIG. 2. Rather, the hole (102-2) in the die (100-2) that is to be connected to the electrode (123) is smaller than the connection pad (101-2) of that die (100-2). Consequently, a ring (130) of connection pad material remains around the hole (102-2).

The holes (102-1, 102-3 and 102-4) in the other dice (100-1, 100-3 and 100-4) are larger, e.g., larger than the connection pads on those dice, such that no connection pad material remains round the larger holes (102-1, 102-3 and 102-4). This may be achieved by drilling a hole larger than the connection pad and thereby completely removing the connection pad from the die. Additionally or alternatively, other chemical or mechanical processes may be employed to completely remove the connection pad material from the vicinity of the hole drilled through that die.

As a result, when the conductive epoxy (121) is applied in the aligned holes (102) of the stack, the epoxy (121) contacts and makes an electrical connection (122) with the connection pad material (130) on the second die (100-2) in the stack and, at bottom, with the electrode (123) on the substrate (120). While the epoxy (121) does contact the other dice in the stack, there is no connection pad material left near the hole on those dice. Consequently, the integrated circuits on those dice (100-1, 100-3, 100-4) are electrically isolated from the column of conductive epoxy (121) and are, therefore, not electrically connected to the electrode (123).

It should be appreciated that if another of the dice (100) was to be selectively connected to the electrode (123), the size of the hole (102) in that die could also be made smaller than the connection pad (101) on that die so that the column of epoxy would also make electrical contact with the circuitry on that die as well as the circuitry on the second die (100-2). In this way, individual dice in the stack can be selectively connected to the larger circuit (123) on the substrate (120) simply by controlling the size of the hole drilled through the connection pad in each die.

Figure 4:
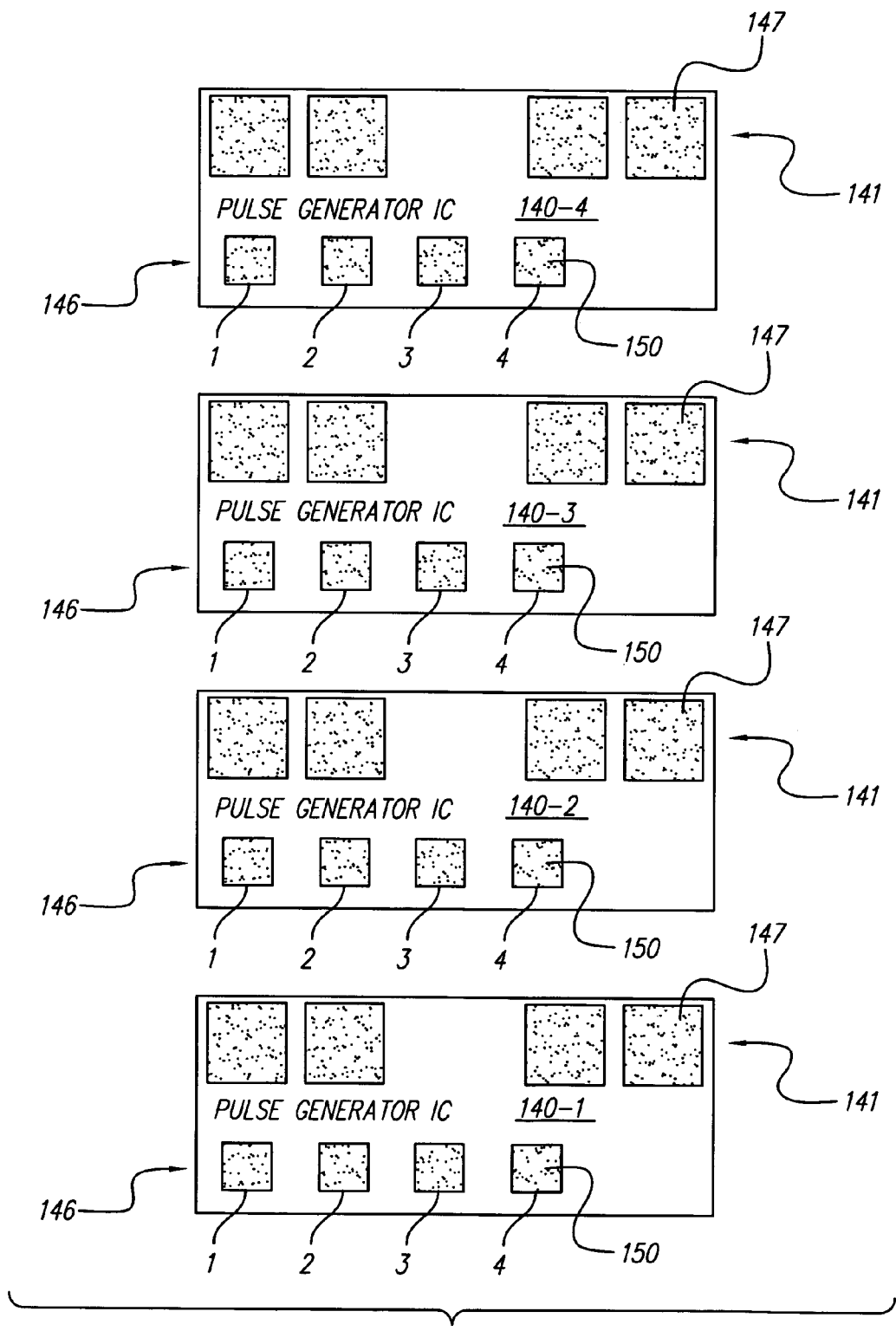
FIG. 4 is an illustration of four integrated circuits that are to be stacked according to principles described herein.

FIG. 4 is an illustration of four integrated circuit (IC) dice that are to be stacked according to principles described herein. These dice (140, i.e., 140-1 to 140-4) are to be combined into a four channel stimulator, each die (140) providing one channel of pulses for the stimulator. The four dice (140) will each be connected to a common digital control IC and a single voltage regulator IC. Each pulse generator IC (140) may be identified from the others by either a mask programmable address, Electrically-Erasable Programmable Read-Only Memory (EEPROM) cells or some other device so that each die (140) may be programmed or accessed independently.

As shown in FIG. 4, each pulse generator IC (140) includes two rows of connection pads, an upper row (141) of larger connection pads (147) and a lower row (146) of smaller connection pads (150). The connection pads (147) of the upper row (141) will be used to connect each of the IC's (140) in the stack to the common digital control IC and the common voltage regulator IC. The connection pads (150) of the lower row (146) will be used to selectively provide an output line or channel, one from each of the ICs (140) in the stack.

Consequently, according to the principles described above, the connection pads (147) in the upper rows (141) will be drilled with progressively smaller holes, but with some connection pad material being left around the hole at each level. In each of the lower rows (146) of connection pads (150), one of the pads (position 1–4) will be drilled with a ring of connection pad material left around the drilled hole. In each IC (140), a different pad (150, 1–4) will have the ring of connection pad material left around the drilled hole. All the other connection pads (150) in the lower rows (146) will be completely ablated or removed by drilling or other processing.

Figure 5:
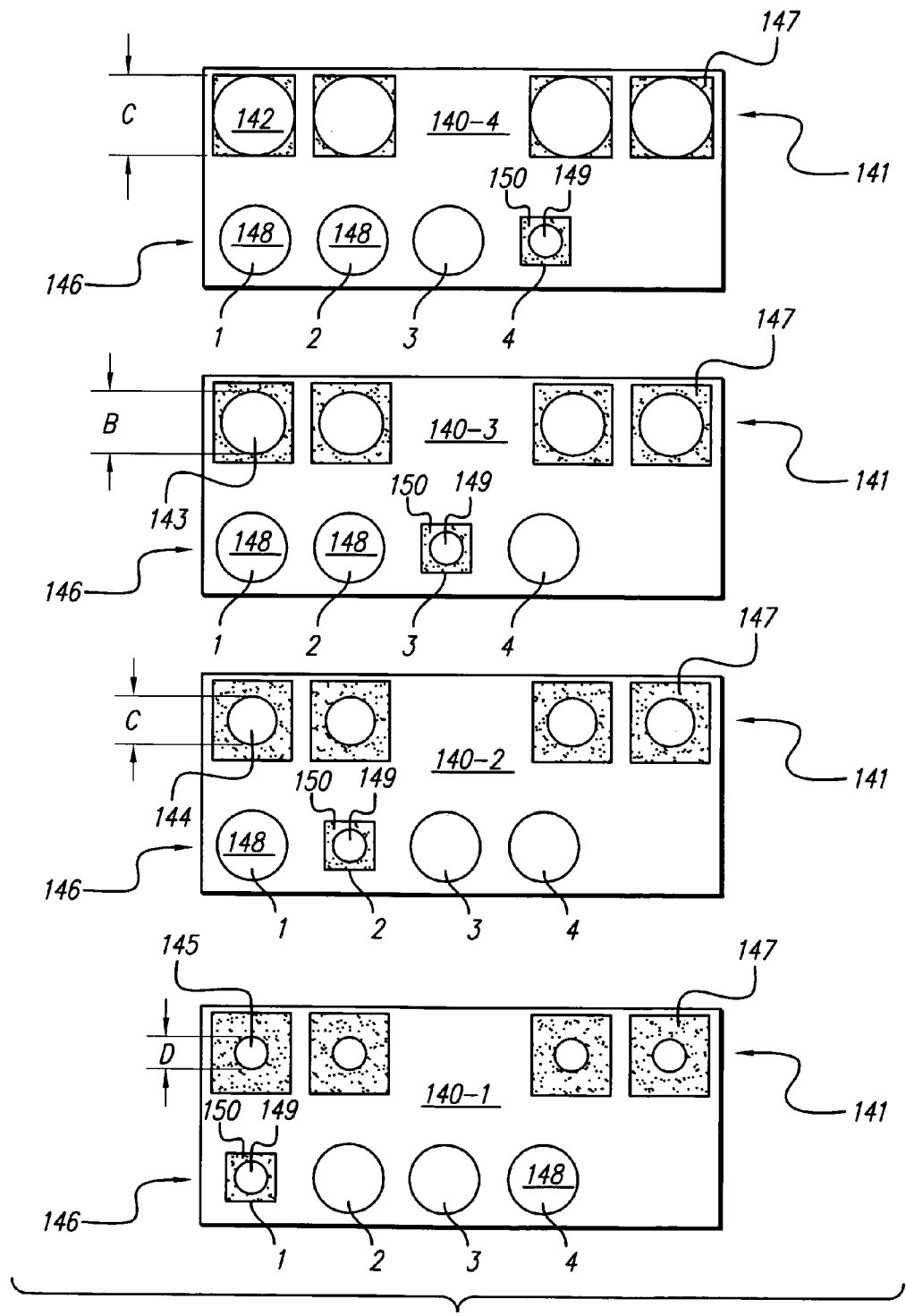
FIG. 5 is an illustration of the four integrated circuits of FIG. 4 after preparations for stacking and for selective and common connections have been made according to principles described herein.

FIG. 5 is an illustration of the four integrated circuits of FIG. 4 after the preparations for stacking and for selective and common connections have been made according to principles described herein. As shown in FIG. 5, starting at the top of the figure, the top pulse generator IC (140-4) has a large hole (142) (diameter A) drilled through each of the connection pads (147) in the top row (141). In the lower row (146) of connection pads (150), large holes (148) have been drilled to completely remove the corresponding connection pads, except at position (4) where a smaller hole (149) has been drilled, leaving a ring of connection pad material (150) around the hole (149).

Moving down the stack, the next pulse generator IC (140-3) has a smaller hole (143) (diameter B) drilled through each of the connection pads (147) in the upper row (141). The diameter (B) of the holes (143) is smaller than the diameter (A) of the holes in the same row (141) of pads (147) in the IC (140-4) above. In the lower row (146) of connection pads (150), large holes (148) have been drilled to completely remove the corresponding connection pads, except at position (3) where a smaller hole (149) has been drilled, leaving a ring of connection pad material (150) around the hole (149).

The next pulse generator IC (140-2) has a still smaller hole (144) (diameter C) drilled through each of the connection pads (147) in the upper row (141). The diameter (C) of the holes (144) is smaller than the diameter (B) of the holes in the same row (141) of pads (147) in the IC (140-3) above. In the lower row (146) of connection pads (150), large holes (148) have been drilled to completely remove the corresponding connection pads, except at position (2) where a smaller hole (149) has been drilled, leaving a ring of connection pad material (150) around the hole (149).

The bottom pulse generator IC (140-1) has the smallest hole (145) (diameter D) drilled through each of the connection pads (147) in the upper row (141). The diameter (D) of the holes (145) is smaller than the diameter (B) of the holes in the same row (141) of pads (147) in the IC (140-2) above. In the lower row (146) of connection pads (150), large holes (148) have been drilled to completely remove the corresponding connection pads, except at position (1) where a smaller hole (149) has been drilled, leaving a ring of connection pad material (150) around the hole (149).

With the four ICs (140) prepared as shown in FIG. 5, the stack can be assembled to form the desired four-channel stimulator. When the four ICs (140) are stacked, a column of conductive epoxy, as described above, will be placed through the holes drilled in the upper and lower rows of conductive pads.

The conductive epoxy deposited through the holes (142 to 145) in the upper rows (141) will make an electrical connection with conductive pad material on each of the ICs (140-1 through 140-4). In contrast, each column of conductive epoxy deposited in a set of registered holes in the lower rows (146) will make an electrical connection with only one of the ICs (140). For example, a column of conductive epoxy deposited through the holes at position (1) in the lower row (146) will only make an electrical connection with the bottom IC (140-1) where a ring of conductive pad material (150) remains around the hole (149) at position (1). Similarly, a column of conductive epoxy deposited through the holes at position (2) in the lower row (146) will only make an electrical connection with the IC (140-2) where a ring of conductive pad material (150) remains around the hole (149) at position (2). A column of conductive epoxy deposited through the holes at position (3) in the lower row (146) will only make an electrical connection with the IC (140-3) where a ring of conductive pad material (150) remains around the hole (149) at position (3). Lastly, a column of conductive epoxy deposited through the holes at position (4) in the lower row (146) will only make an electrical connection with the top IC (140-4) where a ring of conductive pad material (150) remains around the hole (149) at position (4).

Figure 6:
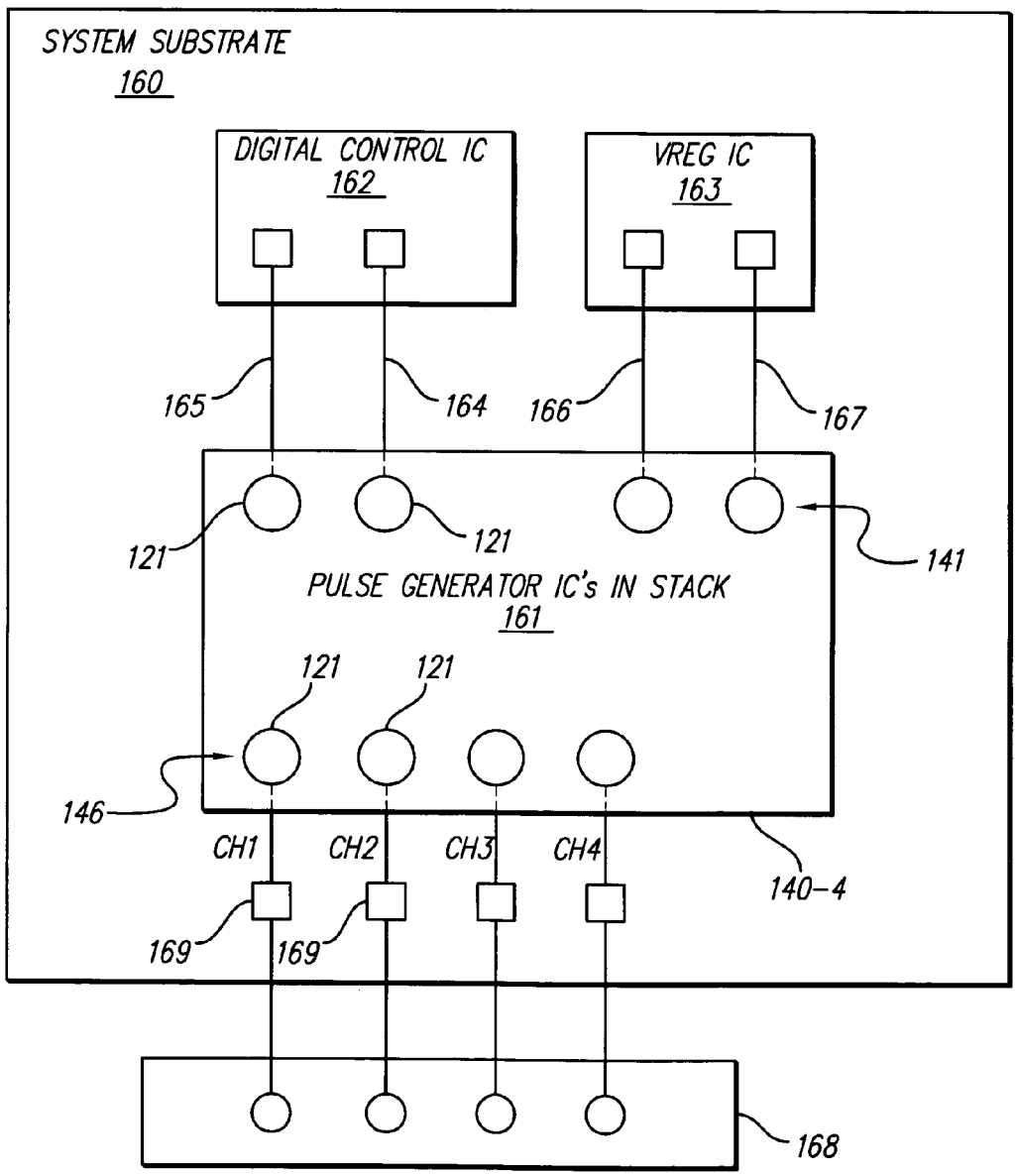
FIG. 6 is an illustration of the resulting stack of integrated circuits installed on a system substrate and connected to a larger circuit according to principles described herein.

FIG. 6 is an illustration of the resulting stack of integrated circuits installed on a system substrate and connected to a larger circuit, i.e., a four-channel stimulator, according to principles described herein. As shown in FIG. 6, a column of conductive epoxy (121) is deposited through each of the holes in the upper row (141). As described above, this epoxy makes an electrical connection with each of the ICs in the stack (161) so as to connect each IC in the stack (161) with underlying electrodes on the system substrate (160). Specifically, a digital control IC (162) has a data line (165) and a clock line (164). A voltage regulator IC (163) has a voltage line (VDD, 167) and a ground line (GND, 166). Each of the columns of conductive epoxy (121) in the holes of the upper row (141) makes an electrical connection between each of the ICs (140) in the stack (161) and a respective one of the data line (165), clock line (164), ground line (166) or voltage line (167). Thus, each die (140) in the stack (161) is connected to and shares the common digital control IC (162) and voltage regulator IC (163).

In contrast, each of the columns of conductive epoxy (121) in the lower row of holes (146) makes electrical contact with only one of the four dice (140) in the stack (161). Thus, each of the four columns of conductive epoxy (121) in the lower row of holes (146) makes a connection between a respective one of the dice (140) in the stack (161) and a respective channel output line (CH1 through CH4). The output lines (CH1-CH4) are each connected to a connection pad (169) so that the four-channel stimulator can be connected to a connector (168) for use in, for example, a medical implant or micro stimulator.

Consequently, as described herein, by controlling the size of holes drilled or cut in the connection pads of a set of dice, the dice can be stacked with conductive epoxy or other conductive material making selective electrical connection to one, two, more or all of the dice in the stack. This allows stacking of the dice to be readily accomplished, even if the dice are of the same size and geometry, thereby realizing a significant advantage in the footprint and density of the resulting circuit.

This method assumes that the die hole and backing are not conductive or can be made such by processes such as coating and secondary drilling. Further customization of the IC dice could be made to obtain independent dice with the same footprints. For example, four independent dice could be made on a mask set that had metallization layers that set the channel output pad and address of the devices. Conductive epoxy or other materials could be applied to the wafers after they had been drilled en-masse allowing surface finishing methods to prepare each IC die to be stacked prior to singulation and assembly into the stack. Ansiotropic elastomeric interposers could be used in place of the conductive epoxy to make connections between the stack elements. The general principle of accurately drilling and either leaving or ablating die pad metallization would apply to all of these methods and the dice so manufactured could have the same dimensions, irrespective of the method used to make the stack.

The preceding description has been presented only to illustrate and describe embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A method of stacking dice in an electronic circuit said method comprising:

controlling a size of a hole made in a connection pad on each die of said dice to selectively provide an electrical connection to a particular die in the stack;

drilling a first hole in a first connection pad of a first die, said first hole being smaller than said first connection pad; and drilling a second hole in a second connection pad of a second die, said second hole being larger than and removing said second connection pad.

2. The method of claim 1, further comprising:

stacking said first and second dice with said first and second holes aligned;

placing conductive material through said first and second holes, said conductive material making an electrical connection to said first connection pad, but not to said second connection pad.

3. The method of claim 2, wherein said conductive material comprises a conductive epoxy.

4. The method of claim 1, wherein said drilling is preformed with a laser.

5. A method of stacking dice in an electronic circuit, said method comprising:

forming holes in each of said dice;

providing electrical connection material selectively at some of said holes to provide for selective electrical connections among said dice;

drilling a first hole in a first connection pad of a first die, said first hole being smaller than said first connection pad; and drilling a second hole in a second connection pad of a second die, said second hole being larger than and removing said second connection pad.

6. The method of claim 5, further comprising:

stacking said first and second dice with said first and second holes aligned;

placing conductive material through said first and second holes, said conductive material making an electrical connection to said first connection pad, but not to said second connection pad.

7. The method of claim 6, wherein said conductive material comprises a conductive epoxy.

* * * * *

UNITED STATES PATENT AND TRADEMARK OFFICE
CERTIFICATE OF CORRECTION

| | | |
|---|---|---|
| PATENT NO. | : 7,211,510 B2 | Page 1 of 1 |
| APPLICATION NO. | : 10/937149 | |
| DATED | : September 9, 2004 | |
| INVENTOR(S) | : Paul Milton Meadows | |

It is certified that error appears in the above-identified patent and that said Letters Patent is hereby corrected as shown below:

Column 8, Line 59, Claim 4 change "whereIn said drilling is preformed..." to --wherein said drilling is preformed...--

Signed and Sealed this

Third Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 7,211,510 B2
APPLICATION NO. : 10/937149
DATED : May 1, 2007
INVENTOR(S) : Paul Milton Meadows It is certified that error appears in the above-identified patent and that said Letters Patent is hereby corrected as shown below:

Column 8, Line 59, Claim 4 change "whereIn said drilling is preformed..." to --wherein said drilling is preformed...--

This certificate supersedes Certificate of Correction issued July 3, 2007.

Signed and Sealed this

Thirty-first Day of July, 2007

JON W. DUDAS
*Director of the United States Patent and Trademark Office*